United States Patent [19]

Tehrani et al.

[11] Patent Number: 4,545,904

[45] Date of Patent: Oct. 8, 1985

[54] APPARATUS FOR REDUCING TAILING IN A LIQUID CHROMATOGRAPH

[75] Inventors: Abolghassem Y. Tehrani; John N. Jones; Robert W. Allington, all of Lincoln,, Nebr.

[73] Assignee: ISCO, Inc., Lincoln, Nebr.

[21] Appl. No.: 585,298

[22] Filed: Mar. 1, 1984

[51] Int. Cl.⁴ .............................................. B01D 15/08
[52] U.S. Cl. .............................. 210/96.1; 210/198.2; 422/70
[58] Field of Search .......................... 210/198.2, 96.1; 422/70; 436/161

[56] References Cited

U.S. PATENT DOCUMENTS

| | | | |
|---|---|---|---|
| 3,440,864 | 4/1969 | Blume | 210/198.2 |
| 3,978,575 | 9/1976 | Beyer | 210/198.2 |
| 4,451,365 | 3/1984 | Sattler | 210/198.2 |
| 4,462,962 | 7/1984 | Baba et al. | 422/70 |

OTHER PUBLICATIONS

Liquid Chromatography, a catalog by Rainin Inst. Co., Woburn, Ma. 1982, p. 16.

Primary Examiner—John Adee
Attorney, Agent, or Firm—Vincent L. Carney

[57] ABSTRACT

To reduce tailing, the frit at the outlet to the liquid chromatographic column has a diameter substantially equal to that of the inside diameter of the outlet end of the column and less than 2 millimeters. It is held directly against the packing of the column within a cylindrical member having a shoulder with a central aperture at least the size of the diameter of the frit and cylindrical walls which are fastened to resist force in the direction of the axis of the column from its inlet to its outlet. A gasket seals the cylindrical holder against the column wall.

14 Claims, 5 Drawing Figures

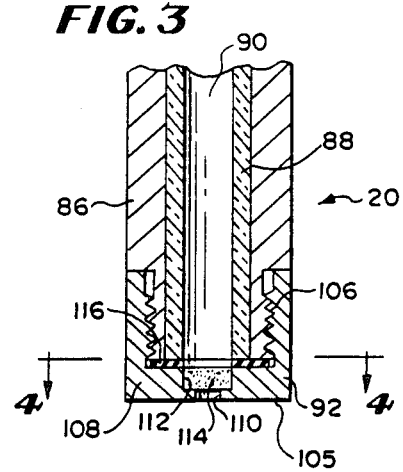
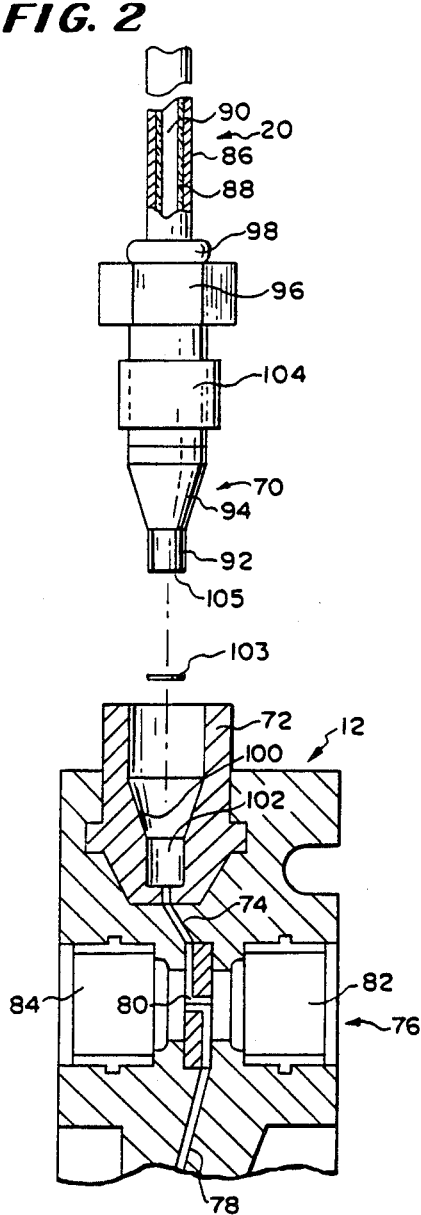
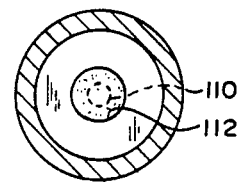
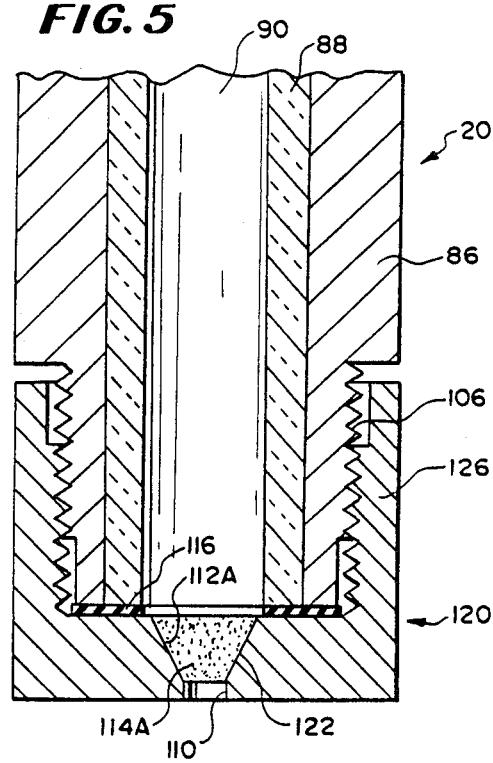

APPARATUS FOR REDUCING TAILING IN A LIQUID CHROMATOGRAPH

BACKGROUND OF THE INVENTION

This invention relates to liquid chromatographic columns and more particularly to fittings for holding the frit in place at the outlet of the column.

It is known to hold the packing in place in a liquid chromatographic column with a porous frit, which has sufficient stiffness and strength to hold the packing against substantial thrust pressure during operation of the chromatograph. The frit is held in place by a threaded fitting.

In a first prior art fitting of the known class the frit is held by a threaded sleeve having a tapered swage or conical surface against which the column is sealed by threaded pressure. The frit has diameter substantially equal to the outer diameter of the column.

In a second prior art fitting of the known class, the frit is held in a plastic ring, such as Kel-F ring, so the frit matches the inner diameter of the column.

The first prior art fitting has several disadvantages, such as: (1) the liquid extends through the frit beyond the inside diameter of the column and this causes some tailing; and (2) the seal is at the tapered joint and thus liquid may flow to that point, causing further tailing. The second type of fitting also has a disadvantage in that, if the plastic ring is compressed with use, or if the plastic ring or frit are too large or too small causing the seal around the column to open, liquid fills the cracks and voids to create tailing.

SUMMARY OF THE INVENTION

Accordingly, it is an object of the invention to provide a novel liquid chromatograph.

It is a further object of the invention to provide a novel chromatograph with reduced tailing caused by the method of mounting of the fittings to the chromatograph.

It is a still further object of the invention to provide a novel frit fixture for holding the frit at the end of the column of a chromatograph.

It is a still further object of the invention to provide a novel apparatus for mounting a chromatograph column.

In accordance with the above and further objects of the invention, a chromatographic column having an inner diameter of less than 2 millimeters has a fastening means on its bottom which cooperates with a frit sleeve. The frit sleeve has a complementary fastening means that permits it to be fastened to the column and hold a frit not substantially larger than the inner diameter of the column and has an opening in its bottom for accommodating the eluent from the column for passage directly through the frit into a flow cell.

A washer is positioned around the end of the column underneath its cylindrical wall to provide a liquid seal between the frit sleeve and near the outlet of the frit sleeve. The frit may be press-fit in a cylindrical opening at the bottom of the sleeve aligned with the inlet to the flow cell or may be bonded in place or fastened within a metal ring or tapered from the outlet of the column to the size of the inlet of the flow cell.

From the above description, it can be understood that the fittings of this invention have the advantages of: (1) having less dead space for the accumulation of fluid at the outlet of the chromatographic column; (2) providing a positive seal between the column and the frit sleeve; and (3) permitting the column to operate with less tailing.

SUMMARY OF THE DRAWINGS

The above noted and other features of the invention will be better understood from the following detailed description when considered in connection with the accompanying drawings, in which:

FIG. 2 is a fragmentary, exploded, partly broken-away elevational view of a portion of the embodiment of the invention of FIG. 1;

FIG. 3 is an enlarged, fragmentary, sectional view of a portion of the embodiment of FIG. 2;

FIG. 4 is a sectional view through lines 4—4 of FIG. 3 of a portion of the embodiment of FIG. 3; and FIG. 5 is a fragmentary, sectional view of another embodiment of the portion of the embodiment of FIG. 2 shown in FIG. 3.

DETAILED DESCRIPTION

Figure 1:
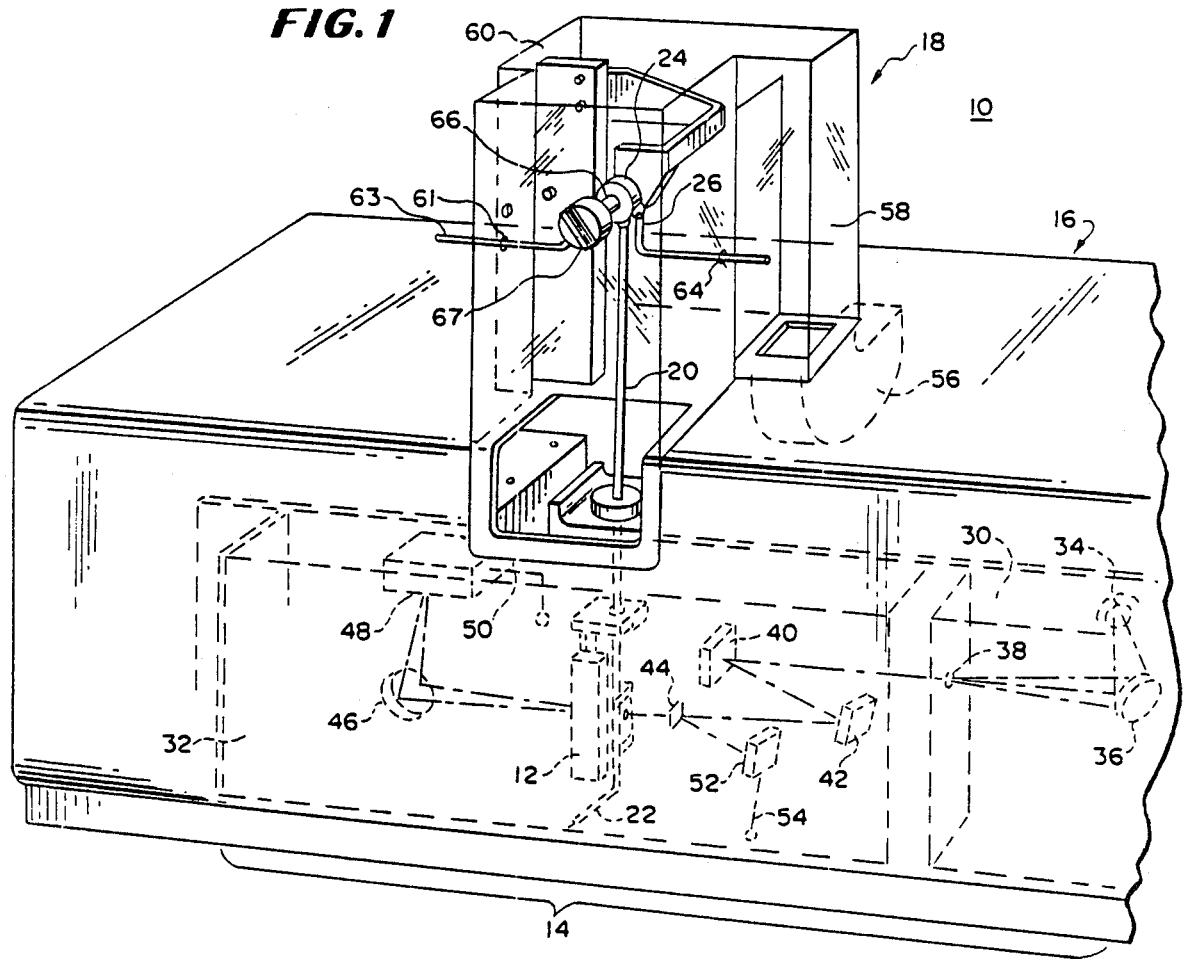
FIG. 1 is a fragmentary, simplified perspective view in accordance with an embodiment of the invention.

In FIG. 1, there is shown a simplified perspective view of a liquid chromatograph 10 having a flow cell assembly 12, a light path assembly 14, an electro-optical section 16 and an air flow control section 18. The light path assembly 14 generates and transmits light through the flow cell assembly 12 within the electro-optical section 16 while the air flow control section 18 controls the flow of air outside of the electro-optical section.

This apparatus 10 is a micro-liquid chromatograph. Micro-liquid chromatography is a form of high performance liquid chromatography that differs from conventional high performance liquid chromatography in that the inside diameter of the column is substantially less than the usual four to five millimeters, the flow rates are less than the usual one to five milliliters per minute, effluent detector volume is less than the usual four to 20 microliters and sample sizes are less than the usual 20 microliters. On the other hand, micro-scale chromatographs have internal column diameters of two millimeters or less, sample sizes less than five microliters and effluent detector volumes less than four microliters.

The flow cell assembly 12 is connected at its top end to a liquid chromatographic column 20 and at its bottom end to an eluate outlet 22. At the upper end of the column 20 is: (1) a sample injection valve 24 for applying samples to the chromatograph for analysis; and (2) a high pressure eluent inlet 26 from a source of eluent which is generally at ambient temperature.

The chromatograph itself may be of any type but the perferred embodiment is directed to a micro-scale, high performance liquid chromatograph such as that described in copending patent application Ser. No. 300,567 filed by Robert W. Allington on Sept. 9, 1981 and assigned to the same assignee as this application.

The light path assembly 14 includes a lamp assembly 30 and an optical compartment 32 mounted side-by-side so that light from the lamp assembly 30 is transmitted to the optical compartment 32 where it is caused to flow through the flow cell assembly 12 within the optical compartment 32. The lamp assembly itself is not part of this invention except insofar as it cooperates with the flow cell assembly 12. However, it includes a lamp 34 and an aspheric condensing mirror 36 which focuses light through a small slit at 38 into the optical compartment 32.

The optical compartment 32 includes an aspheric monochrometer focusing mirror 40, a diffraction grating assembly 42 and a beam splitter 44, which cooperates to transmit a portion of the light through the flow cell assembly 12 for reflection by a collecting mirror 46 onto a first detector 48 which generates a signal on conductor 50 and to focus a second portion of the light focused on a second detector 52 resulting in a signal on conductor 54. These signals are used to provide information about the sample as described in the below mentioned patent and as known in the art.

The electro-optical section 16 includes both the lamp assembly 30 and the optical compartment 32 as well as the electronic equipment necessary for a typical absorbance monitor resulting in output signals that provide information about the eluate flowing through the eluate outlet 22.

The absorbance monitor in the preferred embodiment is similar to the one disclosed in U.S. patent application Ser. No. 351,193 filed in the name of Robert W. Allington on Feb. 22, 1982, entitled "ABSORBANCE MONITOR", and assigned to the same assignee as this application. However, the absorbance monitor has been modified to accommodate the chromatographic column and flow cell within the cabinet in the manner shown in FIG. 1 in the preferred embodiment. The specific absorbance monitor is not part of this invention.

The air flow control section 18 includes a blower 56, and air duct 58 and an air chamber 60. The air chamber 60 encloses the top of the liquid chromatographic column 20, the sample valve 24 and the eluent inlet 26. The walls of the air chamber 60 contain a first opening at 64 through which the eluent inlet 26 passes and a second opening 66 through which the sample valve 24 may be manipulated with knob 67.

In FIG. 2, there is shown an exploded, fragmentary elevational view, partly broken away, of the flow cell assembly 12, the end fitting 70 and the liquid chromatographic column 20, with the flow cell assembly 12 and a portion of the liquid chromatographic column 20 being sectioned. The end fitting 70 mounts to the flow cell assembly 12 directly so that the liquid chromatographic column 20 is in close proximity to the inlet of the flow cell assembly 12. The end fitting 70 is mounted to the liquid chromatographic column 20 and holds the frit.

The flow cell assembly 12 includes an inlet connector 72, an inlet channel 74, an optical assembly 76 and an outlet channel 78. The inlet connector 72 receives the fluid from the liquid chromatographic column 20 and channels it into the inlet channel 74, from there to the optical assembly 76 and then through the outlet channel 78.

The optical assembly 76 includes a light channel 80 connected at one end to the inlet channel 74 and at the other end to the outlet channel 78 and aligned with window assemblies 82 and 84 so that light passing through the light channel 80 passes through the effluent and may be monitored. With this structure, the end of the liquid chromatographic column 20 is less than 30 millimeters from the light channel 80 and preferably less than 15 millimeters with an inlet channel 74 of less than 25 millimeters and preferably less than 15 millimeters to the light channel 80 to minimize the band broadening of the peaks.

The liquid chromatographic column 20 has steel cylindrical outer walls 86 and a glass cylindrical inner lining 88 inside the steel cylindrical outer wall 86, adapted to contain within its center, packing material 90 in a manner known in the art. The liquid chromatographic column 20 is adapted to receive solvents for the elution of molecular species and must withstand high pressure in high performance liquid chromatographs.

The end fitting 70 includes a frit sleeve 92, a ferrule 94, a ferrule nut 96 and a retainer "O" ring 98. There is a similar end fitting 70 on the opposite end of the liquid chromatographic column 20 adapted to cooperate with a sample injector. The frit sleeve 92 is mounted at the end of the liquid chromatographic column 20 and has an outer end surface 105, spaced from it by less than fifty thousandths of an inch. It contains a central aperture aligned with the central passageway of the glass cylindrical inner lining 88 of the liquid chromatographic column 20. The central aperture of the frit sleeve contains, in the preferred embodiment, the frit press-fitted therein.

In the preferred embodiment, the frit has a thickness of less than 65 thousandths of an inch and the end of the frit sleeve 92 is slightly more than distance from the end of the liquid chromatographic column 20 to reduce the distance of fluid flow and thus reduce the broadening of the peak.

The ferrule 94 is adapted to fit within the inlet connector 72 and conforms in its outer diameter to the ferrule opening at 100 which receives it in a tight engaging fit. The frit sleeve 92 extends into a conforming opening 102 in the inlet connector 72 and rests against a gasket 103 which has a central opening slightly larger than the inlet channel 74. The ferrule nut 96 can be threaded downwardly and move the sleeve portion 104 against the walls of the connector 72 to hold the ferrule 94 in place, thus pressing the gasket 103 between the end 105 of the frit sleeve and the bottom wall of the conforming opening 102 forming a liquid light seal. The retainer "O" ring 98 prevents the ferrule nut 96 from rattling when it is loose.

With this configuration, the liquid chromatographic column 20 and end fitting 70 are inserted into the inlet connector 72 with the frit sleeve 92 fitting within a conforming opening 102 and having the central opening in the end surface 105 aligned with the inlet channel 74 for fluid to pass therethrough.

The ferrule 94 in one position loosely engages the walls of the ferrule opening 100 but is moved tightly against them by rotation of the ferrule nut 96. This forces the sleeve 104 into the ferrule 94, expanding it outwardly against the sides to tightly grip the inlet connector 72. The ferrule nut 96 and sleeve 104 are sold by Valco Instruments, P.O. Box 55603, Houston, Tex., under the part number ZN2. In this position, effluent flows through the liquid chromatographic column 20 directly from its outlet through a short thickness of frit into the inlet 74 and from there into the light channel 80 over a relatively short narrow path.

The flow cell 12 may be the type described in copending application for "Chromatographic Flow Cell and Method of Making It", filed by Robert W. Allington and John N. Jones on Mar. 1, 1984, now U.S. patent application Ser. No. 585,347, the disclosure of which is incorporated herein by reference. The invention of this application provides special advantages when used with a flow cell according to the aboveidentified copending application to Allington et al because of the small inlet channel therein.

In FIG. 3, there is shown an enlarged fragmentary sectional view of the frit sleeve 92 and the liquid chromatographic column 20 showing the packing material 90, the glass cylindrical inner lining 88 and the steel cylindrical column wall 86 recessed to form an annular shoulder with external threads at 106 around its lower cylindrical outer wall engaging inner threads along the inner portion of the cylindrical wall of the frit sleeve 92.

As shown in this view, the frit sleeve 92 has an inwardly extending end portion 108 forming an annular shoulder, a central recess 112 containing a frit at 114 and a central outlet 110 in the end 105. The annular inner shoulder supports a washer-shaped gasket 116 which engages the glass cylindrical inner lining 88 and a portion of the steel cylindrical wall 86 on its top and the annular shoulder on the bottom to form a liquid seal. The outer cylindrical wall of the frit sleeve 92 when threaded onto the end of the liquid chromatographic column 20 has its outer cylindrical surface flush with the surface of the column wall 86.

The central outlet 110 is centered in the recess 112 which receives the frit disk 114. The frit disk 114 is of stainless steel particles scintered together to form a porous disk as known in the art. The frit disk 114 is press-fitted into the recess 112. The annular gasket 116 extends beyond the edge of the recess 112 a short distance and forms a seal between the end of the liquid chromatographic column 20 and the annular shoulder 108 to avoid the flow of liquid between the column wall and the frit sleeve 92 while permitting fluid to flow directly through the central outlet 110 into the inlet 74 (FIG. 2) of the flow cell assembly 12.

As shown in FIG. 4, the central outlet 110 is approximately one-fourth the diameter of the frit disk 114 and no greater than two-thirds the inside diameter of the column and, in the preferred embodiment, no greater than 2 millimeters. The frit holding recess 112 has a diameter equal to or slightly smaller than the inside diameter of the column and, in the preferred embodiment, should be no greater than 65 thousandths of an inch which corresponds to the size of the frit with the frit having a thickness of 20 thousandths of an inch in the preferred embodiment and no larger than 100 thousandths of an inch.

Instead of a counterbore through the bottom of a cup-like compartment to hold the frit as shown at 112, a stainless steel ring may fit within a cup about an opening in a thinner bottom and have mounted in its center a frit.

In FIG. 5, there is shown another embodiment of frit sleeve 120 engaging a liquid chromatographic column 20 and having a central outlet 110 similar to that of the embodiment of frit sleeve 92 shown in FIGS. 2-4. The liquid chromatographic column 20 is identical and similar parts are mounted in a similar manner except that the central outlet 110 is adapted to the packing material 90 in size by a conical or truncated cone 122 instead of the cylindrically shaped frit recess 112. The frit 114A is formed within the funnel shaped recess 112A to hold the packing material 90.

The frit 114A is formed to grip the walls of the conical 122 solidly and extends from the central outlet 110 sized to the inlet channel 74 (FIG. 2) upwardly to the packing material 90 conforming on one end to the outlet 110 and at the other to the inside diameter of the column 20. The frit 114A is bonded to the walls of the recess 112A to prevent packing from flowing or the gasket may have a smaller aperture and thus extend over and seal the recess. With this configuration, the streamlined flow reduces band spreading within the frit.

Although a preferred embodiment of the invention has been described with some particularity, many modifications and variations in the preferred embodiment are possible without deviating from the invention. Therefore, it is to be understood that, within the scope of the appended claims, the invention may be practiced other than as specifically described.

What is claimed is:

1. An apparatus comprising:
a chromatographic column having an inner diameter of no more than 2 millimeters;
said chromatographic column having a cylindrical externally threaded recessed portion in its outer wall at least at one end;
cylindrical tubular sleeve means having internal threads adapted to cooperate with the external threads on said column;
said sleeve means having an annular shoulder in its interior;
said annular shoulder being adapted to form a cylindrical opening less than 65 thousandths of an inch in diameter;
said cylindrical opening having a frit therein, whereby packing may be held against substantial thrust forces in the column;
the thickness of said frit being less than one hundred thousandths of an inch;
fastening means for fastening said sleeve to an inlet of a flow cell;
said inlet having a diameter less than two millimeters;
a light channel in said flow cell;
said inlet communicating with the light channel in the flow cell;
the fluid path between the end of said frit and said light channel being less than 15 millimeters; and
said light channel being at right angles to the central axis of said column.

2. An apparatus comprising:
a chromatographic column;
said chromatographic column having a portion in its wall at least at one end with first fastening means thereon;
sleeve means having second fastening means adapted to cooperate with the first fastening means;
an opening in said one end;
said opening having a stiff porous member therein, whereby packing may be held against substantial thrust forces in the column;
the inner diameter of said column being no more than two millimeters;
a flow cell having a light path and inlet for communicating with said opening;
the distance between said opening and said flow cell being less than 15 millimeters;
a shoulder adjacent to said opening;
sealing means for sealing said shoulder to the wall of said chromatographic column;
said shoulder being an annular shoulder around said opening and aligned with said wall of said column.

3. An apparatus according to claim 2 in which said light channel is at right angles to the central axis of said column.

4. An apparatus according to claim 3 in which the stiff porous member is a cylindrical frit having a diameter less than 65 thousandths of an inch.

5. An apparatus according to claim 4 in which the frit is less than 100 thousandths of an inch thick.

6. An apparatus according to claim 2 in which the frit is less than 100 thousandths of an inch thick.

7. An apparatus comprising:
a chromatographic column;
said chromatographic column having a portion in its wall at least at one end with first fastening means thereon;
sleeve means having second fastening means adapted to cooperate with the first fastening means;
an opening in said one end;
said opening having a stiff porous member therein, whereby packing may be held against substantial thrust forces in the column;
the inner diameter of said column being no more than two millimeters;
a flow cell having a light path and inlet for communicating with said opening;
the distance between said opening and said flow cell being less than 15 millimeters; and
the stiff porous member being a cylindrical frit having a diameter less than 65 thousandths of an inch.

8. An apparatus according to claim 7 in which the firt is less than 10 thousandths of an inch thick.

9. A fitting for connecting a chromatographic column to a flow cell having a first diameter and a second diameter defining an annular shoulder between them and an outlet to a flow cell adapted to be aligned with an inlet to the flow cell comprising:
a top side, a bottom side and tubular side walls between the top side and bottom side;
a first fitting opening in the top side having a diameter conforming to the second diameter of the column; the edge of said tubular walls conforming to the interior shoulder defining a first inner diameter of said column outlet, whereby said first fitting opening conforms substantially to said column outlet; and
said bottom side having fitting opening substantially the size of the inlet to the flow cell; said fitting being adapted to hold a frit within the tubular wall, whereby the packing in the chromatorgraphic column may be held in place.

10. A fitting according to claim 9 in which the first and second openings have diameters of less than 2 millimeters and the distance between them is less than 65 thousandths of an inch.

11. A fitting according to claim 10 in which a frit is confined between said first and second openings.

12. A fitting according to claim 9 in which the first and second openings have different sizes and the frit is shaped to conform to each.

13. A fitting according to claim 9 in which the frit is shaped as a truncated cone whereby it has two end surfaces adapted to conform to different size first and second openings.

14. A fitting according to claim 9 further comprising means for fastening said fitting to a chromatographic column with said first opening adjacent to the outlet of said chromatographic column.

* * * * *